United States Patent
Kang et al.

(10) Patent No.: US 9,539,238 B2
(45) Date of Patent: Jan. 10, 2017

(54) PHARMACEUTICAL COMPOSITION COMPRISING A BIGUANIDE DERIVATIVE AS AN ACTIVE INGREDIENT FOR PREVENTING OR TREATING GLIOBLASTOMA

(71) Applicant: ImmunoMet Therapeutics, Inc., Houston, TX (US)

(72) Inventors: Seok Gu Kang, Suwon-si (KR); Ji Hyun Lee, Goyang-si (KR); Jong Hee Chang, Seoul (KR); Jae Ho Cheong, Seoul (KR); Jun Jeong Choi, Incheon (KR); Sung Wuk Kim, Seongnam-si (KR); Sang Hee Yoo, Daejeon (KR); Hong Woo Kim, Daejeon (KR); Soon Im Lee, Seoul (KR)

(73) Assignee: IMMUNOMET THERAPEUTICS, INC, Houston, TX (US)

( * ) Notice: Subject to any disclaimer, the term of this patent is extended or adjusted under 35 U.S.C. 154(b) by 0 days.

(21) Appl. No.: 15/154,788

(22) Filed: May 13, 2016

(65) Prior Publication Data

US 2016/0331724 A1 Nov. 17, 2016

(30) Foreign Application Priority Data

May 13, 2015 (KR) .................. 10-2015-0066845

(51) Int. Cl.
*A01N 43/52* (2006.01)
*A61K 31/40* (2006.01)
*A61K 31/495* (2006.01)

(52) U.S. Cl.
CPC ............ *A61K 31/40* (2013.01); *A61K 31/495* (2013.01)

(58) Field of Classification Search
CPC ..................................................... A61K 31/40
USPC ........................................................ 514/393
See application file for complete search history.

(56) References Cited

U.S. PATENT DOCUMENTS

2014/0179660 A1\* 6/2014 Kim .................. C07D 205/04
514/210.01

OTHER PUBLICATIONS

"Metformin selectively targets cancer stem cells, and acts together with chemotherapy to block tumor growth and prolong remission", Heather A. Hirsch et al., Cancer Research. Oct. 1, 2009; 69(19): 7507-7511.
"Metformin against TGFβ-induced epithelial-tomesenchymal transition (EMT): From cancer stem cells to aging-associated fibrosis", Silvia Cufi et al., Cell Cycle. 2010; 9(22):4461-4468.
"Clinical Implementation of Cancer Energy Metabolism Targeted Therapy", Jae-Ho Cheong, M.D./Ph.D. & "Preclinical trial example: Inhibiting stemness and invasion property of glioma cancer cell by biguanides" Seok-Gu Kang, (2014) M.D./Ph.D.

\* cited by examiner

*Primary Examiner* — Nizal Chandrakumar
(74) *Attorney, Agent, or Firm* — John P. White; Cooper & Dunham LLP (57) ABSTRACT

The present invention provides novel uses of a biguanide derivative for preventing or treating glioblastoma. The compound of Formula 1 and its pharmaceutically acceptable salts can be used for preventing and treating glioblastoma. Further, the combined treatment of the compound of Formula 1 and temozolomide can provide superior effects compared to the administration of the compound of Formula 1 alone or temozolomide alone.

7 Claims, 11 Drawing Sheets

GSC11 x200 Scale bar: 50μm

X01 x200 Scale bar: 50μm

PHARMACEUTICAL COMPOSITION COMPRISING A BIGUANIDE DERIVATIVE AS AN ACTIVE INGREDIENT FOR PREVENTING OR TREATING GLIOBLASTOMA

CROSS-REFERENCE TO RELATED APPLICATIONS

This application claims priority of Korean Patent Application No. 10-2015-0066845, filed May 13, 2015, the contents of which is hereby incorporated by reference in its entirety.

TECHNICAL FIELD

The present invention relates to a use of a biguanide derivative for preventing or treating glioblastoma.

BACKGROUND ART

Glioblastoma (GBM) is the most fatal brain tumor, showing a very limited survival rate in spite of best treatment. Standard first line therapy is a surgery followed by concurrent temozolomide (TMZ) treatment and radiation. According to NCCN guidelines of central nervous system cancer, only a third of patients survive for one year and less than 5% live beyond 5 years. Temozolomide, an alkylating (methylating) agent, is now the standard of care in conjunction with postoperative RT for younger, good performance patients with GBM. However, the patients ultimately succumb to death by the relapse of the disease.

A growing body of evidence that supports the idea that cancers are initiated and maintained by a subpopulation of cells is being reported. The presence of CSCs raises the clinical implication that a curative therapy will require complete elimination of this unique population even in patients with an initial response to treatment, since the disease may ultimately recur if even a small number of CSCs survive the therapy. Accumulated evidence has established that CSC populations are more resistant to conventional cancer therapy than non-CSC populations. For example, CD133 positive GBM CSCs displayed strong capability on tumors' resistance to chemotherapy and radiotherapy. Consequently, novel therapeutic systems have been developed with the purpose of targeting CSCs and altering the microenvironment in which these cells potentially reside. Targeting the surface of markers, signaling cascades, and microenvironments have been tried and examined.

Since studies have unveiled that the biguanide derivate metformin (N',N'-dimethylbiguanide), the most widely used oral therapeutic agent for lowering blood glucose concentrations in patients with type 2 diabetes, significantly reduces cancer incidence and improves cancer patients' survival in type 2 diabetics, laboratory evidence of an antineoplastic effect of biguanide has been accumulated and the first generation of clinical trials on metformin in progress is anticipated. Direct action of biguanides on transformed cells or cells at risk for transformation was attributed to a consequence of homeostatic response to the agent-induced energetic stress or may be attributed to energy depletion by the inhibition of oxidative phosphorylation (OXPHOS), which leads to the energy conservation state or AMPK activation within the cells, but this is still under investigation. Remarkably, Hirsch et al. have demonstrated that mass-forming, self-renewing tumor-initiating breast cancer cells seems to exhibit an exacerbated sensitivity to metformin (Hirsch H A, Iliopoulos D, Tsichlis P N, Struhl K. Metformin selectively targets cancer stem cells, and acts together with chemotherapy to block tumor growth and prolong remission. *Cancer research.* 2009; 69(19):7507-7511). This group suggests that TGF-β-induced EMT might represent a common molecular mechanism underlying the anti-cancer stem cells action of metformin (Cufi S, Vazquez-Martin A, Oliveras-Ferraros C, Martin-Castillo B, Joven J, Menendez J A. Metformin against TGFbeta-induced epithelial-to-mesenchymal transition (EMT): from cancer stem cells to aging-associated fibrosis. *Cell cycle,* 2010; 9(22): 4461-4468,). However, supporting studies for this notion are still limited.

In the present study, we assessed the effect of 1IL56A alone or combined with a previously known agent, temozolomide, on the stem cell properties and survival of orthotopic xenografted animals, to evaluate the feasibility of a new drug, alone or combined with the conventional therapeutic agent TMZ, in the treatment of GBM.

DISCLOSURE OF INVENTION

Technical Problem

The present invention provides use of a biguanide derivative or a pharmaceutically acceptable salt thereof for preventing or treating glioblastoma as an active ingredient.

The present invention provides a method of preventing or treating glioblastoma, comprising administering an effective amount of a biguanide derivative of Formula 1 or a pharmaceutically acceptable salt thereof. The present invention provides a method of preventing or treating glioblastoma, comprising administering the compound of Formula 1 to a subject in need thereof with a therapeutically effective dose.

Solution to Problem

The present invention provides a new use of a biguanide derivative of Formula 1 or a pharmaceutically acceptable salt thereof for preventing or treating glioblastoma; a pharmaceutical composition for preventing or treating glioblastoma, comprising a biguanide derivative of Formula 1 or a pharmaceutically acceptable salt thereof as an active ingredient; and a method of preventing or treating glioblastoma, comprising a step of administering an effective amount of a biguanide derivative of Formula 1 or a pharmaceutically acceptable salt thereof:

Formula 1

The chemical name of the compound of Formula 1 is N—(N-(4-(trifluoromethoxy) phenyl) carbamimidoyl)pyrrolidine-1-carboximidamide. In the present specification, the compound is also called HL156A.

The present invention comprises not only the compound represented by Formula 1 and the pharmaceutically acceptable salt thereof, but also all solvates or hydrates that can be prepared therefrom.

As shown in the following examples, the compound represented by Formula 1 or the pharmaceutically acceptable salt thereof may be useful in preventing or treating glioblastoma.

Accordingly, the present invention provides a pharmaceutical composition for preventing or treating glioblastoma comprising the compound of Formula 1, a use of the compound of Formula 1 or the pharmaceutically acceptable salt thereof for preparing drugs for preventing or treating glioblastoma, and a method for preventing or treating glioblastoma comprising a step of administering a pharmaceutically effective amount of the compound of Formula 1 or the pharmaceutically acceptable salt thereof.

In an embodiment, the pharmaceutical composition is used for combination therapy with temozolomide. In the following experimental examples, the combined treatment of HL156A and temozolomide showed survival benefits in the orthotopic xenograft mouse mode.

Accordingly, the present invention provides a pharmaceutical composition for preventing or treating glioblastoma, comprising a compound of Formula 1 and temozolomide as an active ingredient:

Formula 1

The pharmaceutical composition of the present invention may be formulated in a suitable dosage form for a desired route of administration.

The present invention provides a dosage form comprising a compound of Formula 1 and temozolomide as an active ingredient.

Formula 1

Meanwhile, a pharmaceutically acceptable salt of the compound of Formula 1 according to the present invention may be an acid addition salt formed using an organic acid or an inorganic acid. For example, the organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, difluoroacetic acid, aminooxy acetic acid, benzenesulfonic acid, 4-toluenesulfonic acid, and methanesulfonic acid; and the inorganic acid may include, for example, hydrochloric acid, hydrobromic acid, sulfuric acid, phosphoric acid, nitric acid, carbonic acid, and boric acid.

For example, the above-described acid addition salt may be prepared by a typical method of preparing a salt, including a) directly mixing the compound of Formula 1 and an acid, b) dissolving one of the compound and an acid in a solvent or a hydrated solvent and mixing the resulting solution, or c) mixing the compound of Formula 1 and the acid in the presence of a solvent or a hydrated solvent.

According to one exemplary embodiment, the pharmaceutically acceptable salt of the compound of Formula 1 may be a salt of an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid, and boric acid.

The pharmaceutical composition of the present invention includes at least one pharmaceutically acceptable carrier in addition to the active ingredient. As used in this specification, the term pharmaceutically acceptable carrier refers to a known pharmaceutically acceptable excipient which is useful in formulating a pharmaceutically active compound for administration, and is substantially non-toxic and non-sensitive under the conditions used.

An exact ratio of the excipient is determined by standard pharmaceutical practice, as well as solubility, chemical characteristics, and selected route for administration of the active compound.

The pharmaceutical composition of the present invention may be formulated in a dosage form suitable for a desired administration method using a suitable and physiologically available adjuvant such as an excipient, a disintegrating agent, a sweetening agent, a binder, a coating agent, a swelling agent, a lubricating agent, a glossing agent, a flavoring agent, or the like.

The pharmaceutical composition may be formulated as a tablet, a capsule, a pill, a granule, a powder, an injection, or a liquid, but the present invention is not limited thereto.

The formulation and the pharmaceutically acceptable carrier of the pharmaceutical composition may be properly selected according to the techniques known in the related art, and, for example, may be selected with reference to the following documents: (Urquhart et al., Lancet, 16:367, 1980); (Lieberman et al., PHARMACEUTICAL DOSAGE FORMS-DISPERSE SYSTEMS, 2nd ed., vol. 3, 1998); (Ansel et al, PHARMACEUTICAL DOSAGE FORMS & DRUG DELIVERY SYSTEMS, 7th ed., 2000); (Martindale, THE EXTRA PHARMACOPEIA, 31st ed.); (Remington's PHARMACEUTICAL SCIENCES, 16th-20th editions); (THE PHARMACOLOGICAL BASIS OF THERAPEUTICS, Goodman and Gilman, eds., 9th ed., 1996); and (Wilson and Gisvolds' TEXTBOOK OF ORGANIC MEDICINAL AND PHARMACEUTICAL CHEMISTRY, Delgado and Remers, eds., 10th ed., 1998). Also, principles of formulating a pharmaceutical composition may be described, for example, with reference to the following documents: (Platt, Clin Lab Med, 7:289-99, 1987); (Aulton, PHARMACEUTICS; THE SCIENCE OF DOSAGE FORM DESIGN, Churchill Livingstone, N.Y., 1988); (EXTEMPORANEOUS ORAL LIQUID DOSAGE PREPARATIONS, CSHP, 1998); and (Drug Dosage, J Kans Med Soc, 70(1): 30-32, 1969).

Meanwhile, the term treating includes relieving a symptom, temporarily or permanently eliminating causes of the symptom, and preventing or hindering occurrence of the symptom or progression of the above-described condition, disorder, or disease, but the present invention is not limited thereto.

An effective amount of the active ingredient of the pharmaceutical composition according to the present invention refers to an amount required to treat a disease. Therefore, the effective amount of the active ingredient may be adjusted according to various factors such as kinds and severity of a disease, kinds and contents of an active ingredient and other ingredients included in the composition, kinds of a formulation, age, body weight, general medical conditions, sex, and diet of a patient, duration and route of administration, a release rate of the composition, treatment duration, and the number of drugs used together. In the case of adults, for example, the compound of Formula 1 may be administered in a total dose of 1 to 3,000 mg/kg, preferably 1 to 100 mg/kg, more preferably 10 to 50 mg/kg when administered once to several times a day.

Advantageous Effects of the Invention

The compound of Formula 1 and its pharmaceutically acceptable salts may be used for preventing and treating glioblastoma.

MODE FOR THE INVENTION

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

Materials

Cells

GSC11, established at M.D. Anderson Cancer Center—Houston from primary gliomas removed from glioma patients and the X01 line, derived from a woman with a glioblastoma multiforme were used for experimentation (Jiang H, Gomez-Manzano C, Aoki H, et al. Examination of the therapeutic potential of Delta-24-RGD in brain tumor stem cells: role of autophagic cell death. *Journal of the Notional Cancer Institute*. 2007; 99(18):1410-1414, Soeda A, Park M, Lee D, et al. Hypoxia promotes expansion of the CD133-positive glioma stem cells through activation of HIF-1alpha. *Oncogene*. 2009; 28(45):3949-3959.).

Lentiviral Vector Transduction and Expression

GFP stably expressed GSC11s (G-GSC11) were generated by growing GSC11 cells in complete medium and then applying GFP-expressing lentiviral supernatants. Polybrene (Sigma) was added to a final concentration of 8 μg/ml and incubated with cells for 18 hours. After infection, the cells were placed in fresh growth medium and cultured in a standard manner. Cells were treated with 1 mg/ml puromycin (Life Technologies Korea, Seoul, Korea) to eliminate uninfected cells and generated stable G-GSC11, GFP-expressing GSC11s were isolated for use in further experiments by fluorescence-activated cell sorting (FACS).

The Chemical Structure of HL156A

Figure 1A:
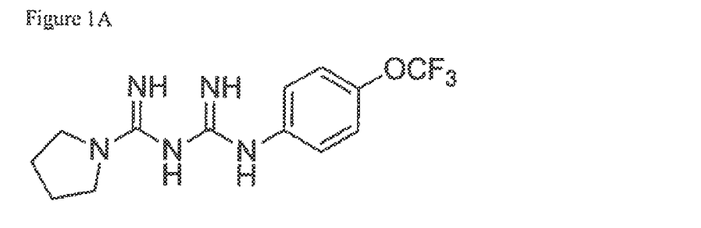
FIG. 1A shows the structure of HL156A(N—(N-(4-(trifluoromethoxy) phenyl) carbamimidoyl) pyrrolidine-1-carboximidamide acetate).

The chemical structure of HL156A (N—(N-(4-(trifluoromethoxy) phenyl) carbamimidoyl)pyrrolidine-1-carboximidamide) is depicted in FIG. 1A. In all experiments, HL156A was used in the form of an acetate salt, a derivative of biguanide with high bioavailability.

Statistical Analysis

Data was analyzed using SPSS for Windows, Version 12.0 (SPSS Inc., Chicago, Ill., USA). Student T-test or Mann-Whitney U-test were used for comparison of mean of viability of FDG uptake of agent-treated cells. Kaplan-Meier survival curves and log-rank statistics were employed for survival analysis. Results were considered statistically significant when P<0.05.

EXAMPLE 1

The Effect of HL156A, TMZ and Combination Treatment on Cell Viability

The effect of HL156A, TMZ, and combined HL156A and temozolomide on the survival of cells was determined by 3-(4,5-dimethylthiazol-2-yl)-2,5-diphenyl tetrazolium bromide (MTT) assay. Cells were seeded in 96-well plates and incubated at 37° C. for 24 hours and treated with HL156A, TMZ, and the combination thereof for 5 days. MTT reagent (10 μl/well) was added, incubated at 37° C. for 4 hours and the absorbance was measured at 490 nm. Each experiment was repeated three times and the results were expressed as % viable cells over control.

Figure 1B:
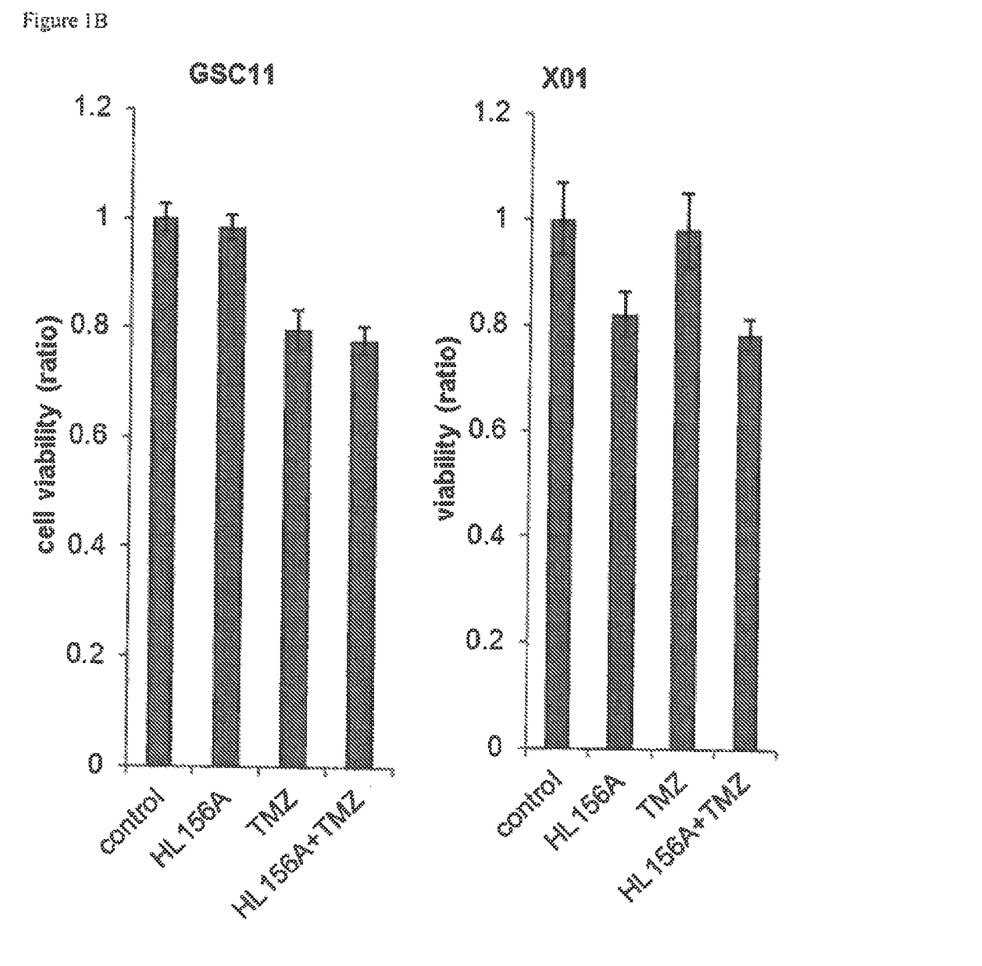
FIG. 1B show the effect of HL156A, TMZ, and combination treatment on stem cell viability. The treatment showed minimal effect on the cell viability.

As a result, the sublethal dose treatment of the agents showed minimal effect on the cells (FIG. 1B). A sublethal dose of each drug was used in pursuing specific cellular phenomenon without killing cells. 15 μM of HL156A and 500 μM of TMZ were adopted for further experiments.

EXAMPLE 2

The Effect of HL156A, TMZ and Combination Treatment on AMPK and mTOR Pathway of GSC11 and X01 Cells For Western blotting, 20 μg total protein from each sample was treated with Laemmli sample buffer and heated at 100° C. for 5 minutes. This was then loaded into each well and was resolved by 8% SDS-polyacrylamide gel electrophoresis (PAGE) and eleetroblotted onto nitrocellulose membranes (GE Healthcare life-Sciences). Membranes were blocked in 5% non-fat dry milk in TBS-T, and incubated with antibodies for AMPK-mTOR pathway-related proteins, stemness markers, and EMT-related markers overnight at 4° C., and then probed with peroxidase-conjugated goat anti-rabbit IgG (1:2000, santa cruz) for 1 hour at room temperature. The washes were repeated and the membrane was developed with a chemiluminescent agent (ECL; Amersham Life Science, Inc.). Band densities were measured using TINA image software (Raytest, Straubenhardt, Germany).

Figure 1C:
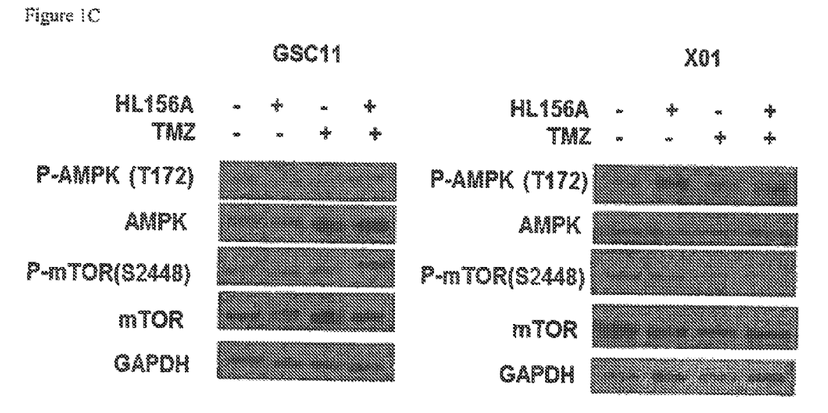
FIG. 1C shows the effect of drugs on AMPK and mTOR pathway (*: Statistically significant, ns: Not statistically significant).

Generally, it is known that biguanide works as an AMPK agonist and consequently, mTOR inhibition follows. However, this was not the case for glioblastoma tumorspheres. mTOR inhibition by AMPK activation was not observed in GSC11 and X01 cells (FIG. 1C). That is, the cellular mechanism underlying the effect of HL156A seems distinctive in that it did not show expected AMPK activation and the consequent mTOR inhibition pathway. The present invention also confirms increased basal AMPK expression in GSC11 and X01 and similarly, AMPK activation and consequent mTOR inhibition is not obvious in the inhibitory effect of HL156A and combined HL156A and TMZ on the glioma tumorspheres.

EXAMPLE 3

The Effect of HL156A, TMZ, and Combination Treatment on the Stemness of Tumorspheres For Neurosphere formation assay, the GSC11 and X01 cells were cultured in medium consisting of DMEM/F-12 with 2% 1×B27, 20 ng/ml 0.02% bFGF, 20 ng/ml 0.02% EGF, and 1% antibiotic-antimycotic solution (100×, Gibco, Invitrogen Korea, Seoul, South Korea). The cells were cultured in different conditions for 3 weeks. Cell cultures were observed with an inverted phase-contrast microscope (1×71 Inverted Microscope; Olympus, Tokyo, Japan) to determine morphology and the size of the tumorsphere. Photographs of cells were obtained with a digital camera (DP70 Digital Microscope Camera; Olympus), using DP Controller software (Olympus).

Figure 2A:
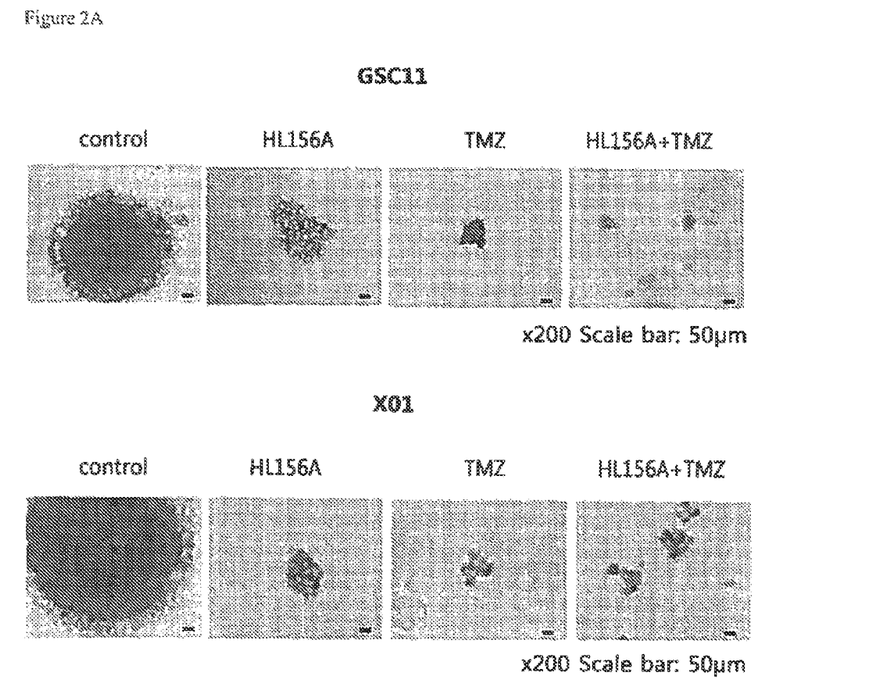
FIGS. 2A and 2B show a drug effect on the stemness assessed by the neurosphere formation assay. The number of neurospheres was decreased on the treatment of HL156A and combined HL156A and TMZ.
Figure 2B:
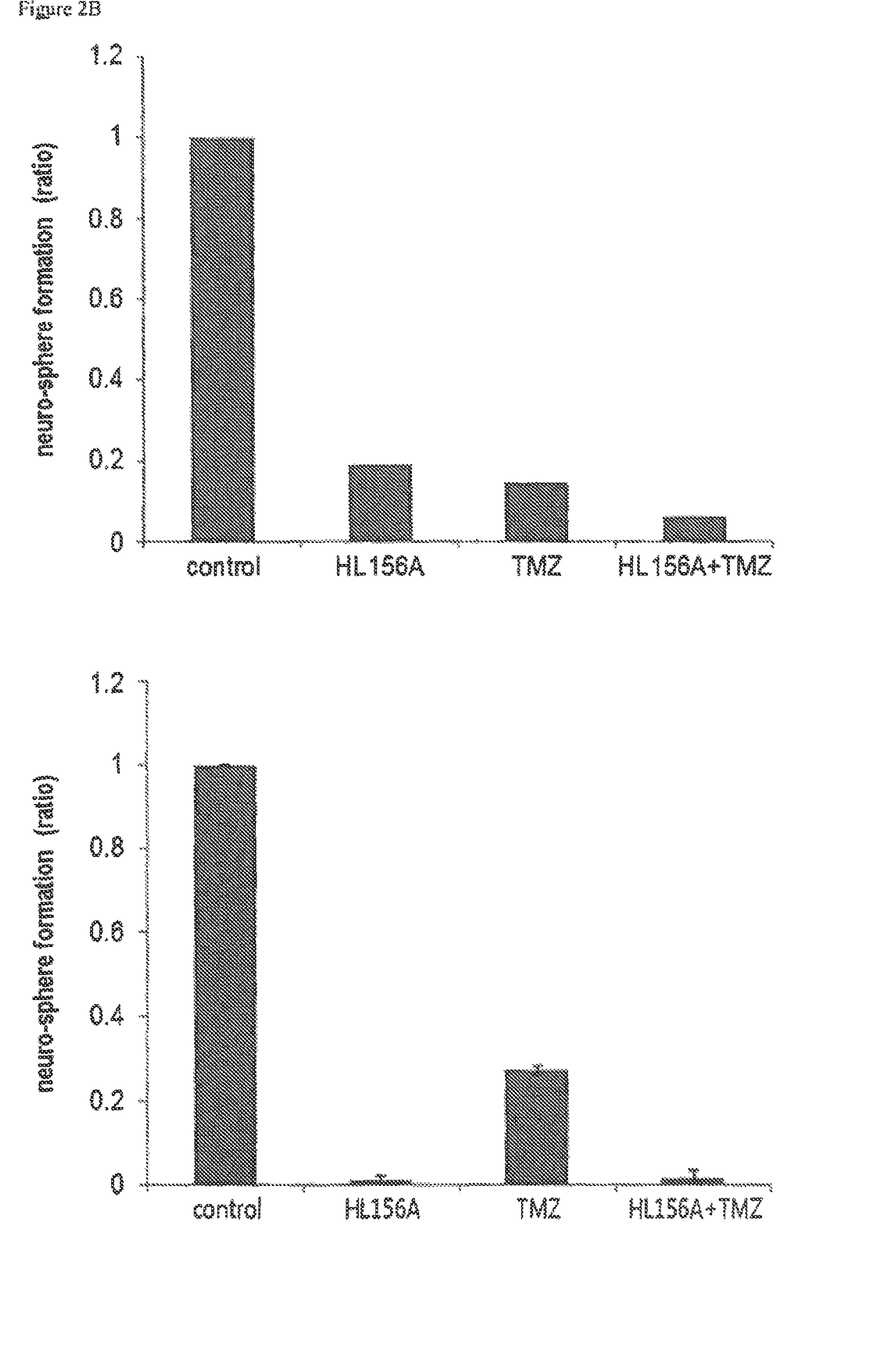
Figure 2C:
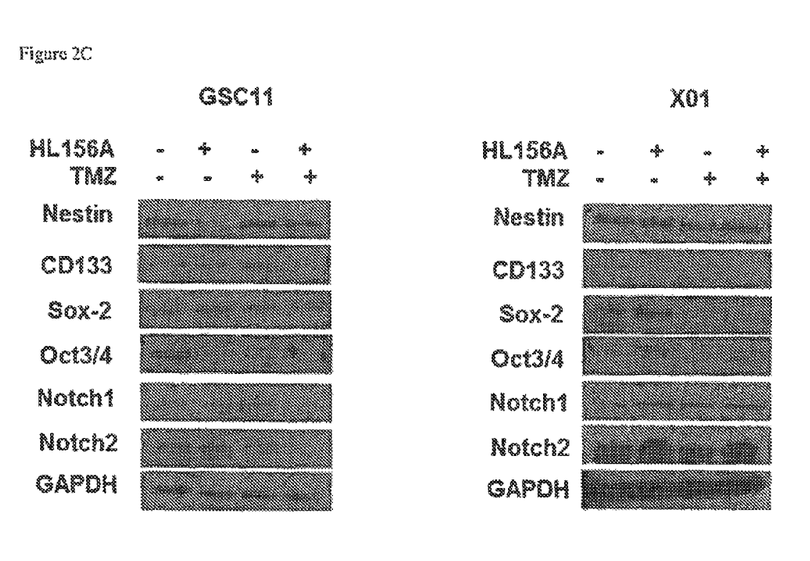
FIG. 2C shows that markers representing stemness, such as CD133 and Sox, were less expressed in the combination treatment group.

As a result, HL156A seems to decrease stemness of GSC11 and X01, proven by neurosphere formation assay (FIGS. 2A and 2B) and western blotting of stemness markers such as nestin, CD133, Sox-2, Notch 1, Notch 2, and Oct3/4. The number of neurospheres was markedly decreased on the treatment of HL156A and this inhibitory effect was most prominent in the combination treatment. Decreased expression of CD133, OCT 3/4, Sox-2, Notch 1, and Notch 2 was observed in either GSC11 or X01 (FIG. 2C).

EXAMPLE 4

The Effect of HL156A, TMZ, and Combination Treatment on Neuro-glial Differentiation of GSC11 and X01

Figure 2D:
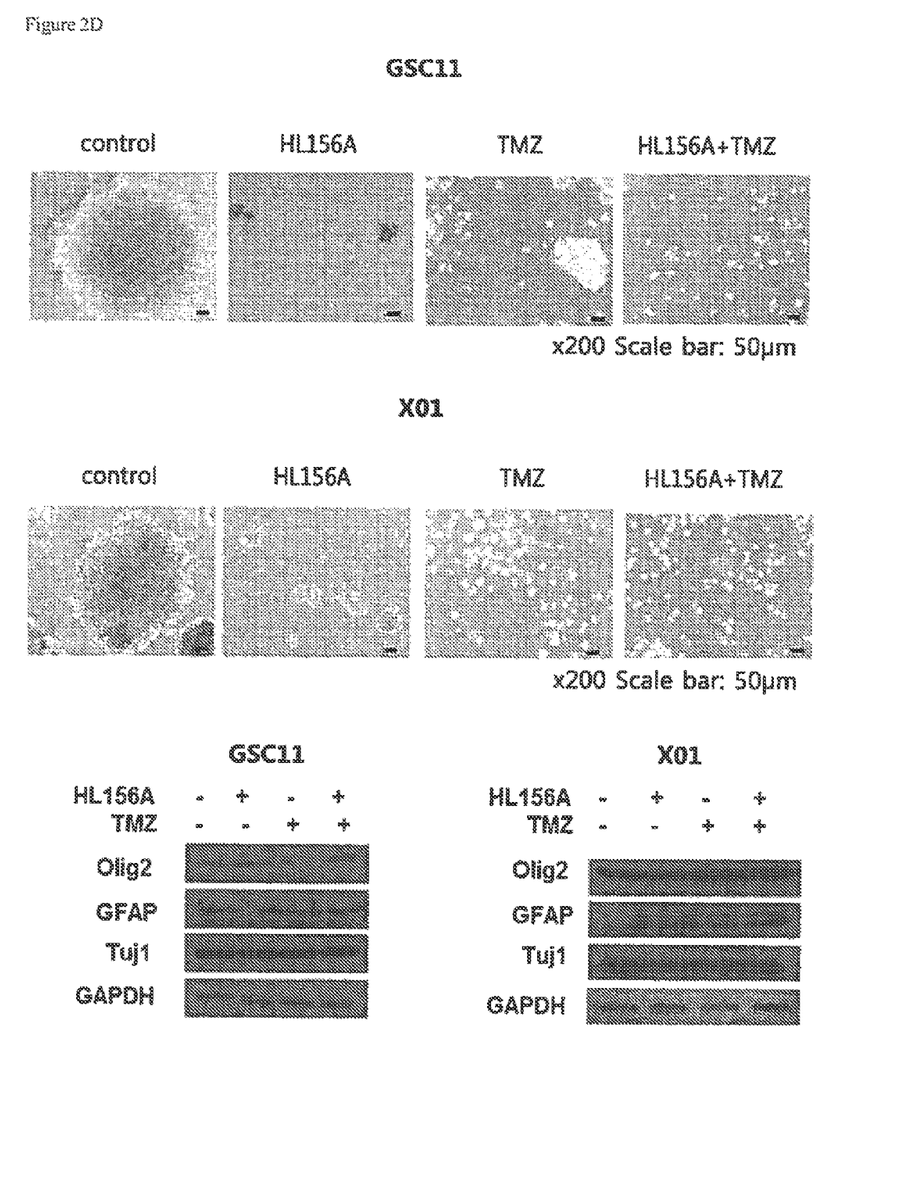
FIG. 2D shows that the treatment did not affect neuroglial differentiation in GSC11 (*: Statistically significant).

Either HL156A or TMZ did not promote neuro-glial differentiation as the expressions of neuronal markers such as olig2, Tuj1, and GFAP were not changed (FIG. 2D). Thus, a therapeutic effect by differentiating tumor cells, which is one of the proposed mechanisms of targeting stem cells, seems not to be the mechanism of the drugs.

EXAMPLE 5

The Effect of HL156A, TMZ, and Combination Treatment on the Invasive Property of GSC11

The G-GSC11s grown in spheroid were cultured in collagen I matrices using polydimethylsiloxane (PDMS)-based micro-wells (diameter and depth of microwells: 6 nm and 500 μm). The microwells were treated with a 1% poly (ethyleneimine) (Sigma-Aldrich, St. Louis, Mo., USA) solution for 10 minutes followed by 0.1% glutaraldehyde (Sigma-Aldrich, St. Louis, Mo., USA) for 30 minutes and washed with PBS overnight lo make PDMS wells adherent to collagen. The 4 mg/ml collagen I matrices are prepared from high-concentration rat tail collagen I (BD Bioscience, CA, USA) using the recommended manual provided by the manufacturer. Briefly, the amounts of 10× phosphate buffered saline (PBS), 1N NaOH, sterile $dH_2O$, and collagen I were mixed to create gels based on the desired final concentration. The solution was well mixed and kept at 4° C. before use. To encapsulate G-GSC11 spheroid, 10 μl of a collagen I solution (4 mg/ml) were pipetted into the microwell, single G-GSC11 spheroid was placed onto collagen I matrices from the culture plate, and 10 μl of a collagen I solution (4 mg/ml) was dropped onto G-GSC11 spheroid. The platform was incubated at 37° C. and 5% $CO_2$ for 30 minutes. The cell viability was characterized by staining G-GSC11 spheroid with 8 μM Ethidium homodimer-1 (Invitrogen Korea, Seoul, South Korea) for 30 minutes at 37° C. before implantation in collagen matrix. After fall gelation, a superlayer of culture medium consisting of DMEM/F-12 with 2% 1×B27, 20 ng/ml 0.02% bFGF, 20 ng/ml 0.2% EGF, and 1% antibiotic-antimycotic solution (100× Gibco, Invitrogen Korea, Seoul, South Korea) was then added. To observe drug effects, drugs were mixed with medium considering the final concentration of each drug. Images were taken using an inverted confocal laser scanning microscope (Nikon Ti-E, Tokyo, Japan) to observe dynamic morphology of G-GSC11 spheroids. To quantitate the invasion assay, the maximal area covered by migrating edges of cells was used as a parameter for defining invasiveness (invaded area at certain time/spheroid area at initial time×100). Data was analyzed through image analysis software ImageJ (NIH, Bethesda, Md., USA).

Figure 3A:
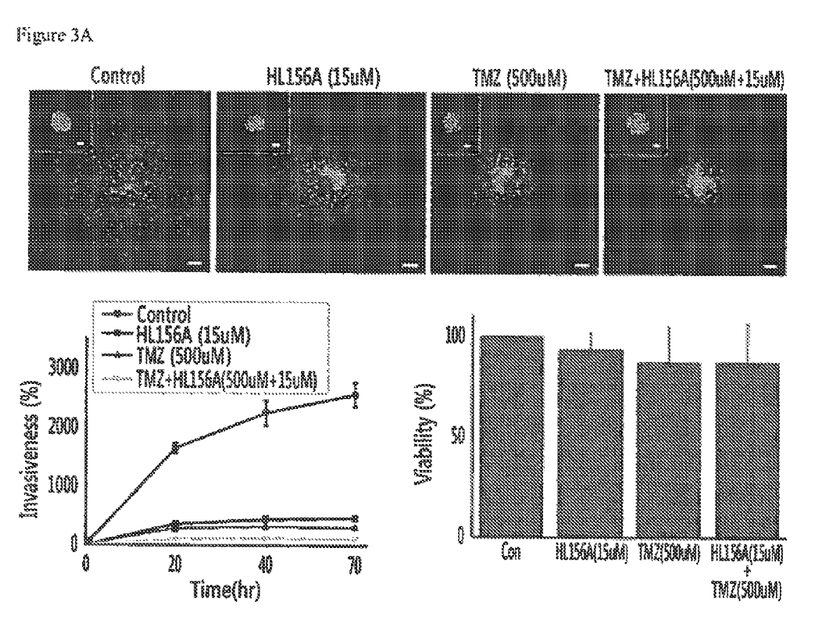
FIGS. 3A and 3B show that the treatment of HL156A and the HL156A and TMZ combination shows decreased invasiveness on 3D collagen matrix invasion assay (A: implanted cells and drugs together, B: pre-implanted, drug treatment after 12 hours).

In 3D invasion assay with collagen I matrix, HL156A exhibited a lesser degree of invasiveness as depicted (FIG.

Figure 3B:
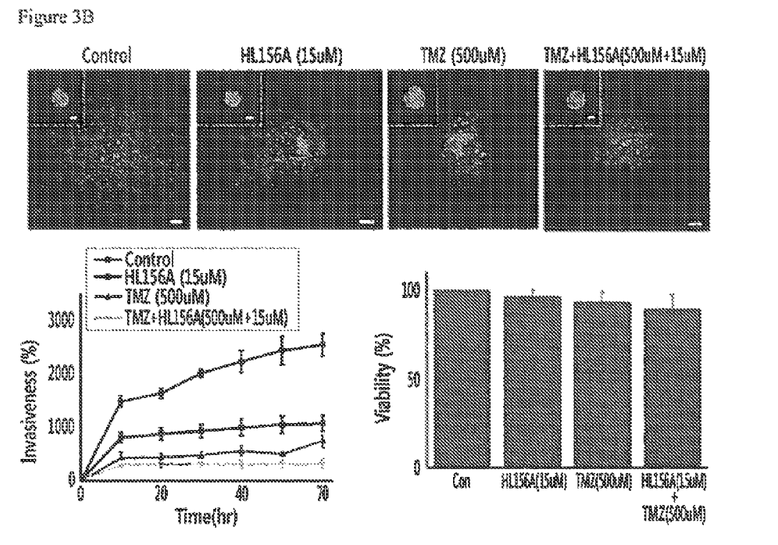
Figure 3C:
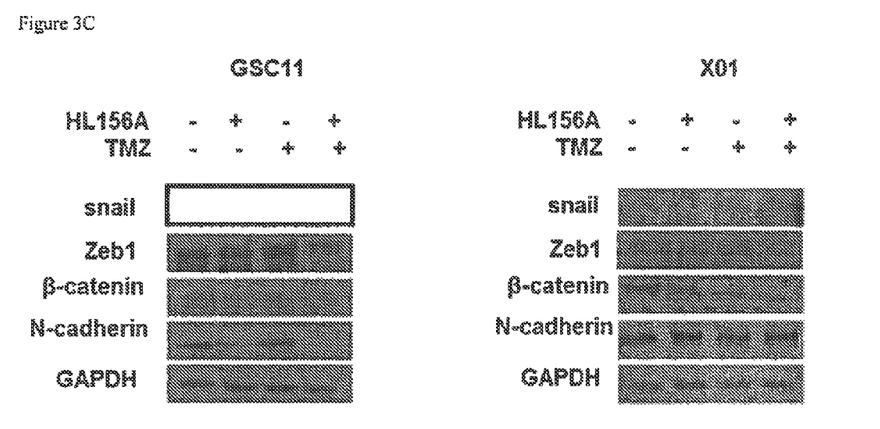
FIG. 3C shows that markers related with EMT pathway were altered on the treatment of HL156A. EMT-related and TGF-β signaling-related marker expression in the individually acquired CSCs revealed that most of samples express genes involving these pathways.

3A, implanted cells and drugs together). It was not because of drug effects on the cell viability, as the cell viability during the experiment was also assessed with no significant cell death. To recapitulate a real clinical situation where a drug is administered to the patient after the tumor formation, the same assay was performed but the treatment of drug was given 12 hours after implantation (FIG. 3B). Even in this setting, the inhibitory effect of invasion was most prominent in the combination treatment. As several groups reported that EMT-related markers were upregulated is GBM and the acquisition of mesenchymal traits by cancer cells undergoing EMT has been reported to be related with the acquisition of a stem cell program (Ortensi B, Setti M, Osti D, Pelicci G. Cancer stem cell contribution to glioblastoma invasiveness. *Stem cell research & therapy* 2013; 4(1):18, Kalluri R, Weinberg R A. The basics of epithelial-mesenchymal transition. *The Journal of clinical investigation,* 2009; 119(6): 1420-1428.), the expression of EMT-related markers such as β-catenin, zeb1, N-cadherin, and snail was assessed, revealing the expression of β-catenin, zeb1, and N-cadherin was diminished on the treatment of HL156A and the combination treatment, suggesting that the agent may perturb the EMT-related pathway in the tumorspheres (FIG. 3C).

EXAMPLE 6

The Assessment of Cellular Metabolism by Analyzing $^{18}$F-FDG Uptake

In order to assess the effect of drugs on the cellular metabolism, $^{18}$F-FDG uptake was examined, GSC11 were plated on 12-well plates with $3\times10^5$ cells per well for 24 hours. The medium was changed to a glucose-free DMEM medium (Gibco, Invitrogen Korea, Seoul, South Korea) containing approximately 0.5 µCi of $^{18}$F-FDG, followed by incubation for 15 minutes. The cells were washed with phosphate-buffered saline 3 times and 0.1 ml of lysis buffer was added to each well. The lysed cells were then harvested to measure the amount of radioactivity by Wallac 148 Wizard 3 gamma-counter (PerkinElmer Life and, Analytical Science, Shelton, Conn., USA). The radioactivity measured was normalized to protein content.

Figure 4A:
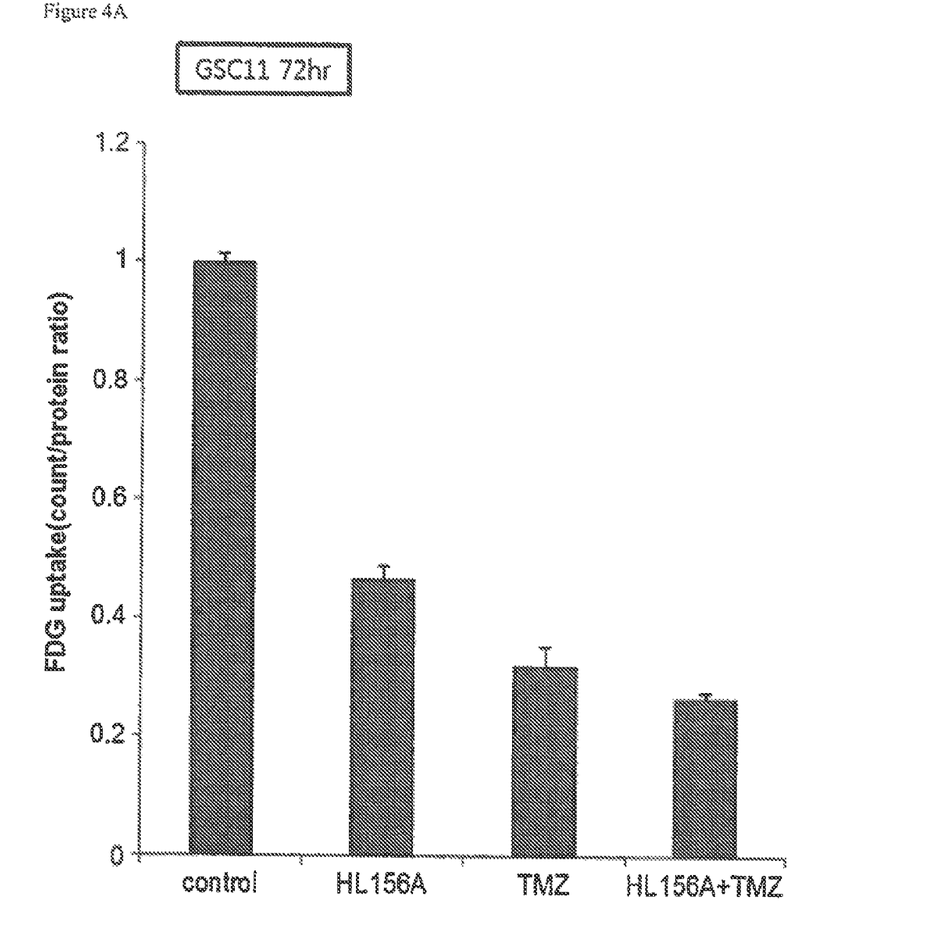
FIG. 4A shows that $F^{18}$-FDG uptake was markedly decreased in HL156A, TMZ and combination treatment. The decrease in FDG uptake was most prominent in the combination treatment group, suggesting low metabolic status (ns: Not statistically significant).

As a result, $^{18}$F-FDG was decreased as cells were treated with drugs and the decrease was most prominent in the combination treatment group. Thus, the drugs seems to decrease cellular metabolism and the degree of inhibition is most obvious in the combination group (FIG. 4A).

EXAMPLE 7

Gene Expression Microarray and Gene Ontology Analysis

Total RNA was extracted from 100 mg of tissue using a Qiagen miRNA kit according to the manufacturer's protocol. Expression profiles of drug treated groups and control were obtained using Illumina HumanHT-12 v4 Expression BeadChip (Illumina, Inc., San Diego, Calif., USA). Data were log 2 transformed and normalized with a quantile normalization method using BRB-ArrayTools developed by Dr. Richard Simon and the BRB-ArrayTools Development Team. Genes showing minimal variation across the set of arrays were excluded from the analysis. Genes whose expression differed by at least 1.5-fold from the median in at least 20% of the arrays were retained. Gene set comparison tools provided by BRB-ArrayTools were used for gene ontology analysis.

Figure 4B:
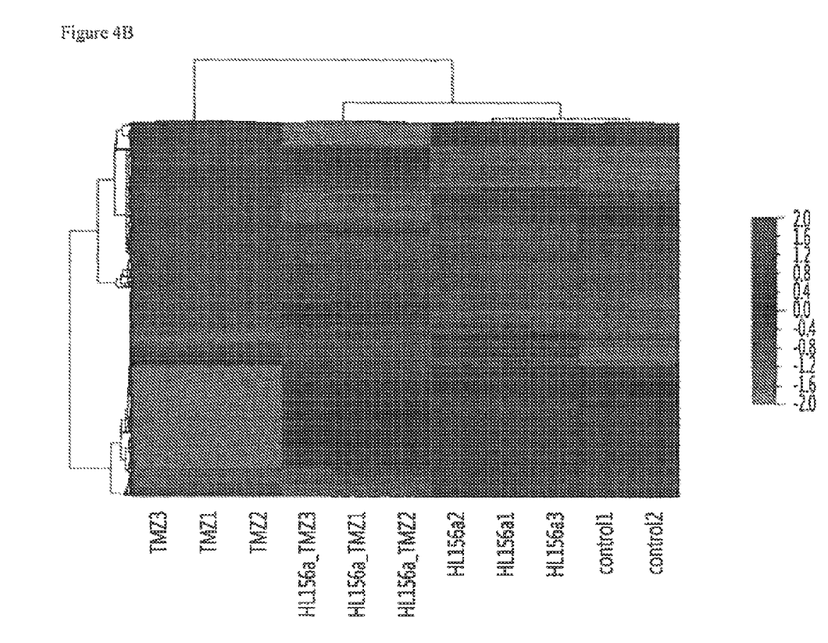
FIG. 4B shows the high throughput gene expression microarray. Gene expression microarray data was subject to gene set enrichment analysis. Sets of genes were differentially expressed in the combination treatment group.

Transcriptome analysis by Illumina HumanHT-12 v4 Expression BeadChip was acquired and a heatmap with hierarchical clustering was generated (FIG. 4B). There are genes differentially expressed when the combination treatment was given, among which several downregulated genes such as FBLN7, an adhesion molecule that interacts with extracellular matrix, Lyn, a molecule known to regulate cell migration, and LAMA4, a type of laminin, were included. When compared to the TMZ single treatment, the combination treatment showed differentially expressed gene sets that include gene sets related to cell adhesion, cell migration, cell motion, and regulation of cell adhesion (Table 1).

TABLE 1

Results of GO analysis

| | GO category | GO ontology | GO term | Number of genes | LS permutation p-value | KS permutation p-value | Efron-Tibshirani's GSA test p-value |
|---|---|---|---|---|---|---|---|
| 1 | GO: 0007155 | BP | cell adhesion | 88 | 0.00003 | 0.24119 | 0.04 (+) |
| 2 | GO: 0022610 | BP | biological adhesion | 88 | 0.00003 | 0.24119 | 0.04 (+) |
| 3 | GO: 0048699 | BP | generation of neurons | 96 | 0.00008 | 0.00622 | <0.005 (−) |
| 4 | GO: 0050839 | MF | cell adhesion molecule binding | 22 | 0.00023 | 0.05207 | 0.11 (+) |
| 5 | GO: 0001558 | BP | regulation of cell growth | 29 | 0.00023 | 0.00411 | <0.005 (+) |
| 6 | GO: 0045595 | BP | regulation of cell differentiation | 92 | 0.00029 | 0.0322 | 0.095 (+) |
| 7 | GO: 0048870 | BP | cell motility | 93 | 0.00035 | 0.15429 | <0.005 (+) |
| 8 | GO: 0051674 | BP | localization of cell | 93 | 0.00035 | 0.15429 | <0.005 (+) |
| 9 | GO: 0016477 | BP | cell migration | 92 | 0.00041 | 0.16148 | <0.005 (+) |
| 10 | GO: 0034330 | BP | cell junction organization | 12 | 0.00044 | 0.00094 | <0.005 (−) |
| 11 | GO: 0030182 | BP | neuron differentiation | 86 | 0.00046 | 0.01401 | <0.005 (−) |
| 12 | GO: 0000902 | BP | cell morphogenesis | 82 | 0.00047 | 0.032 | 0.205 (+) |

TABLE 1-continued

Results of GO analysis

| | GO category | GO ontology | GO term | Number of genes | LS permutation p-value | KS permutation p-value | Efron-Tibshirani's GSA test p-value |
|---|---|---|---|---|---|---|---|
| 13 | GO: 0016337 | BP | single organismal cell-cell adhesion | 28 | 0.0005 | 0.24627 | <0.005 (+) |
| 14 | GO: 0009611 | BP | response to wounding | 68 | 0.0005 | 0.07895 | 0.07 (+) |
| 15 | GO: 0016192 | BP | vesicle-mediated transport | 73 | 0.00061 | 0.00701 | 0.335 (+) |
| 16 | GO: 0048666 | BP | neuron development | 67 | 0.00069 | 0.06203 | <0.005 (−) |
| 17 | GO: 1903035 | BP | negative regulation of response to wounding | 9 | 0.00072 | 0.00408 | <0.005 (+) |
| 18 | GO: 0005178 | MF | integrin binding | 13 | 0.00072 | 0.01091 | <0.005 (+) |
| 19 | GO: 0006897 | BP | endocytosis | 34 | 0.00074 | 0.00291 | 0.435 (+) |
| 20 | GO: 0030155 | BP | regulation of cell adhesion | 34 | 0.00077 | 0.40607 | <0.005 (+) |
| 21 | GO: 0045216 | BP | cell-cell junction organization | 11 | 0.00077 | 0.00179 | <0.005 (−) |
| 22 | GO: 0034097 | BP | response to cytokine | 55 | 0.00078 | 0.10488 | 0.145 (+) |
| 23 | GO: 0007160 | BP | cell-matrix adhesion | 12 | 0.0008 | 0.01404 | <0.005 (−) |
| 24 | GO: 0031348 | BP | negative regulation of defense response | 10 | 0.00082 | 0.00278 | <0.005 (+) |
| 25 | GO: 0098602 | BP | single organism cell adhesion | 32 | 0.00096 | 0.42385 | <0.005 (+) |
| 26 | GO: 0016049 | BP | cell growth | 38 | 0.00099 | 0.11886 | <0.005 (+) |
| 27 | GO: 0030030 | BP | cell projection organization | 74 | 0.001 | 0.06159 | 0.14 (−) |
| 28 | GO: 0032102 | BP | negative regulation of response to external stimulus | 14 | 0.00101 | 0.00215 | 0.12 (+) |
| 29 | GO: 0032989 | BP | cellular component morphogenesis | 86 | 0.00115 | 0.08409 | 0.245 (+) |
| 30 | GO: 0034329 | BP | cell junction assembly | 10 | 0.00117 | 0.00268 | <0.005 (−) |
| 31 | GO: 0050767 | BP | regulation of neurogenesis | 41 | 0.00133 | 0.08463 | 0.21 (+) |
| 32 | GO: 0051093 | BP | negative regulation of developmental process | 51 | 0.00159 | 0.04778 | <0.005 (+) |
| 33 | GO: 0023056 | BP | positive regulation of signaling | 76 | 0.00169 | 0.09863 | <0.005 (+) |
| 34 | GO: 0010647 | BP | positive regulation of cell communication | 77 | 0.00189 | 0.0942 | <0.005 (+) |
| 35 | GO: 0031175 | BP | neuron projection development | 62 | 0.00192 | 0.08327 | 0.08 (+) |
| 36 | GO: 0001952 | BP | regulation of cell-matrix adhesion | 5 | 0.00197 | 0.001 | <0.005 (−) |
| 37 | GO: 0031589 | BP | cell-substrate adhesion | 19 | 0.00206 | 0.2878 | 0.03 (−) |
| 38 | GO: 0043405 | BP | regulation of MAP kinase activity | 18 | 0.00226 | 0.00123 | <0.005 (+) |

TABLE 1-continued

Resalts of GO analysis

| | GO category | GO ontology | GO term | Number of genes | LS permutation p-value | KS permutation p-value | Efron-Tibshirani's GSA test p-value |
|---|---|---|---|---|---|---|---|
| 39 | GO: 0050728 | BP | negative regulation of inflammatory response | 7 | 0.00245 | 0.01371 | <0.005 (+) |
| 40 | GO: 2001237 | BP | negative regulation of extrinsic apoptotic signaling pathway | 9 | 0.00251 | 0.01567 | <0.005 (+) |
| 41 | GO: 0000904 | BP | cell morphogenesis involved in differentiation | 64 | 0.00253 | 0.07539 | 0.08 (+) |
| 42 | GO: 0043588 | BP | skin development | 24 | 0.0026 | 0.06641 | 0.25 (+) |
| 43 | GO: 0007264 | BP | small GTPase mediated signal transduction | 23 | 0.00263 | 0.00184 | 0.21 (−) |
| 44 | GO: 0009897 | CC | external side of plasma membrane | 17 | 0.00271 | 0.49503 | 0.055 (+) |
| 45 | GO: 0051216 | BP | cartilage development | 13 | 0.00324 | 0.01037 | <0.005 (+) |
| 46 | GO: 0045664 | BP | regulation of neuron differentiation | 33 | 0.00344 | 0.18438 | 0.21 (+) |
| 47 | GO: 0007266 | BP | Rho protein signal transduction | 7 | 0.00345 | 0.00382 | <0.005 (−) |
| 48 | GO: 0043406 | BP | positive regulation of MAP kinase activity | 11 | 0.00348 | 0.01644 | <0.005 (−) |
| 49 | GO: 0051960 | BP | regulation of nervous system development | 44 | 0.00351 | 0.26241 | <0.005 (+) |
| 50 | GO: 0061448 | BP | connective tissue development | 17 | 0.00353 | 0.00213 | <0.005 (+) |
| 51 | GO: 0033559 | BP | unsaturated fatty acid metabolic process | 6 | 0.00368 | 0.02054 | <0.005 (+) |
| 52 | GO: 1903034 | BP | regulation of response to wounding | 31 | 0.00371 | 0.48388 | 0.145 (+) |
| 53 | GO: 0006909 | BP | phagocytosis | 11 | 0.00395 | 0.00158 | 0.34 (+) |
| 54 | GO: 0048864 | BP | stem cell development | 16 | 0.00416 | 0.00813 | <0.005 (+) |
| 55 | GO: 0061024 | BP | membrane organization | 44 | 0.00425 | 0.0609 | 0.035 (+) |
| 56 | GO: 0006954 | BP | inflammatory response | 34 | 0.00427 | 0.23222 | 0.145 (+) |
| 57 | GO: 0030054 | CC | cell junction | 80 | 0.00438 | 0.06943 | 0.175 (−) |
| 58 | GO: 0030098 | BP | lymphocyte differentiation | 13 | 0.00448 | 0.00078 | 0.4 (+) |
| 59 | GO: 0048771 | BP | tissue remodeling | 18 | 0.00453 | 0.001 | 0.15 (−) |
| 60 | GO: 0022407 | BP | regulation of cell-cell adhesion | 13 | 0.00458 | 0.0547 | <0.005 (+) |
| 61 | GO: 0032990 | BP | cell part morphogenesis | 59 | 0.00479 | 0.04231 | 0.14 (−) |

Differentially expressed gene sets between TMZ and combination treatment. Expression of several gene sets related cellular adhesion and migration was significantly different between the two groups.

EXAMPLE 8

The Effect of HL156A on the Xenografted Tumor Growth

Finally, the effect of the drags on the tumors of orthotopic xenograft mice was analyzed, 4- to 8-week-old male athymic nude mice (Central Lab. Animal Inc., Seoul, South Korea) were used for experiments. Mice were housed in micro-isolator cages under sterile conditions and observed for at least 1 week before study initiation to ensure proper health. Lighting, temperature, and humidity were controlled centrally. All experimental procedures were approved by Yonsei University College of Medicine Institutional Animal Care and Use Committee. Mice were anesthetized with a solution of Zoletil® (30 mg/kg; Virbac Korea, Seoul, South Korea) and xylazine (10 mg/kg; Bayer Korea, Seoul, South Korea) delivered intraperitoneally. GSC11 were implanted into the right frontal lobe of nude mice using a guide-screw system within the skull. Mice received $5 \times 10^5$ cells via a Hamilton syringe (Dongwoo Science Co., Seoul, South Korea) inserted to a depth of 4.5 mm. Then, 15 mg/kg of HL156A, 66.6 mg/kg of TMZ, and their combination were administrated to mice (n=5 per group). HL156A was given to mice by oral administration every other day until the duration of the experiment and TMZ was administrated intraperitoneally, for 5 days from the day of tumorsphere injection. The body weight of mice was checked every other day. If the weight decreased more than 15% compared to the original body weight, mice were euthanized according to protocol. When mice died, mouse brains were carefully removed and gliomagenesis was observed after generating H-E stained slides.

Figure 5:
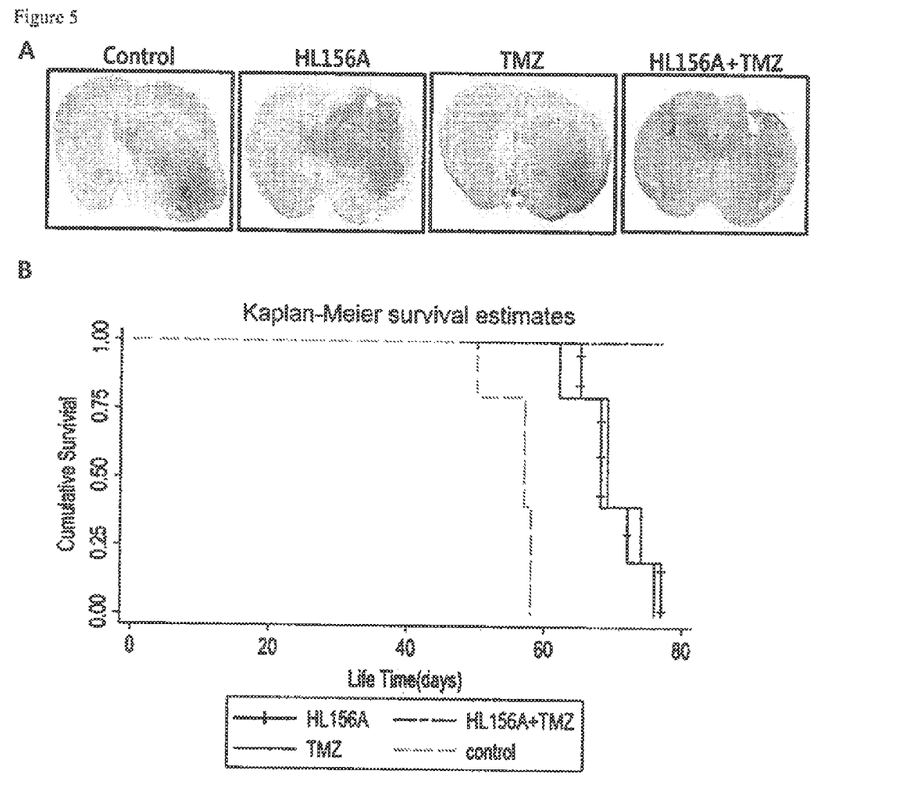
FIG. 5 shows the effect of HL156A and combined HL156A and TMZ on the xenografted tumor growth and survival of animals. (A) Tumors from HL156A, TMZ, and combined HL156A and TMZ were stained and examined. HL156A- and combination-treated animals showed a less irregular margin than that of the control. In particular, the combination-treated group showed a tumor with decreased volume. (B) Survival of combination groups was significantly increased (p=0.0000).

As a result, although the combination treatment did not prevent the formation of the mass, the size end extent of mass was limited in the combination treatment group mice (FIG. 5). It revealed that the treatment of the combination of HL156A and TMZ had a benefit in overall survival of animals (p=0.000, log rank test, FIG. 5B). Particularly, A possible explanation of the superior result of survival in the combination group in this study may be attributed to 1) the TMZ, tumor cytotoxic effect in addition to the deteriorated cellular energy metabolism environment induced by HL156A and 2) the additive inhibitory effect of TMZ and HL156A on the invasive property of tumorspheres, which results in the less aggressive tumor phenotype.

What is claimed is:

1. A method of treating glioblastoma, comprising administering a pharmaceutical composition to a subject in need thereof with a therapeutically effective dose, wherein the composition comprises a compound of Formula 1 below or a pharmaceutically acceptable salt thereof as an active ingredient

[Formula 1]

2. The method according to claim 1, wherein the pharmaceutically acceptable salt is a salt of an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid, and boric acid.

3. The method according to claim 2, wherein the pharmaceutically acceptable salt is a salt of acetic acid.

4. The method according to claim 1, wherein the pharmaceutical composition further comprises temozolomide or a pharmaceutically acceptable salt thereof.

5. The method according to claim 1, wherein the compound of Formula 1 decreases a sternness of cancer stem cells.

6. The method according to claim 1, wherein the composition decreases stemness of cancer stem cells in a subject.

7. The method according to claim 4, wherein the composition decreases stemness of cancer stem cells in a subject.

* * * * *